United States Patent [19]

Martin

[11] Patent Number: 4,833,139
[45] Date of Patent: May 23, 1989

[54] ENHANCING CHOLINERGIC ACTIVITY WITH 5-SUBSTITUTED 1-[4-(1-PYRROLIDINYL)-2-BUTYNYL]-2-PYRROLIDINONES AND RELATED COMPOUNDS

[75] Inventor: Lawrence L. Martin, Lebanon, N.J.

[73] Assignee: Hoechst-Roussel Pharmaceuticals, Inc., Somerville, N.J.

[21] Appl. No.: 217,730

[22] Filed: Jul. 5, 1988

Related U.S. Application Data

[62] Division of Ser. No. 148,268, Jan. 25, 1988, Pat. No. 4,772,601.

[51] Int. Cl.$^4$ ............... A61K 31/40; A61K 31/54; C07D 207/416
[52] U.S. Cl. ............... 514/227.8; 514/235.5; 514/255; 514/326; 514/356; 514/422; 544/60; 544/111; 544/141; 544/372; 546/208; 548/146; 548/518; 548/551
[58] Field of Search ............... 514/227.8, 235.5, 255, 514/326, 356, 422; 544/60, 111, 141, 372; 546/208; 548/146, 518, 551

[56] References Cited

U.S. PATENT DOCUMENTS 4,670,456 6/1987 Weber et al. ............... 514/424

Primary Examiner—Richard A. Schwartz
Assistant Examiner—Richard Sharpe
Attorney, Agent, or Firm—Tatsuya Ikeda

[57] ABSTRACT

There are disclosed compounds of the formula

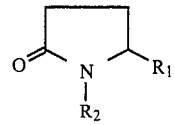

where $R_1$ is loweralkoxycarbonyl, $-CH_2OH$ or $-CONR_3R_4$, $R_3$ and $R_4$ being independently hydrogen, loweralkyl or arylloweralkyl; and $R_2$ is $-CH_2CH=CH_2$,

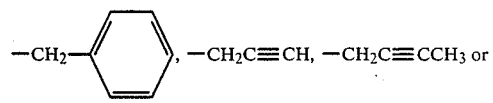

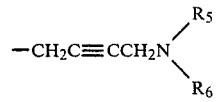

$R_5$ and $R_6$ being independently loweralkyl or alternatively the group $-NR_5R_6$ as a whole being

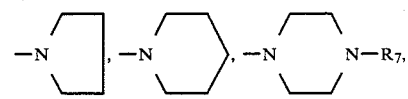

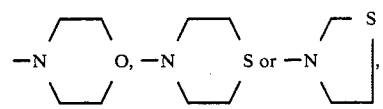

$R_7$ being hydrogen, loweralkyl or arylloweralkyl; which are useful for enhancing cholinergic activity in mammals and hence for the treatment of various memory dysfunctions characterized by decreased cholinergic function such as Alzheimer's disease.

11 Claims, No Drawings

ENHANCING CHOLINERGIC ACTIVITY WITH 5-SUBSTITUTED 1-[4-(1-PYRROLIDINYL)-2-BUTYNYL]-2-PYRROLIDINONES AND RELATED COMPOUNDS

This is a division of application Ser. No. 148,268, filed Jan. 25, 1988, now U.S. Pat. No. 4,772,601.

The present invention relates to compounds of formula I

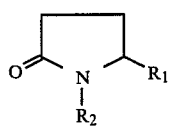

where $R_1$ is loweralkoxycarbonyl, $-CH_2OH$ or $-CONR_3R_4$, $R_3$ and $R_4$ being independently hydrogen, loweralkyl or arylloweralkyl; and $R_2$ is $-CH_2CH=CH_2$,

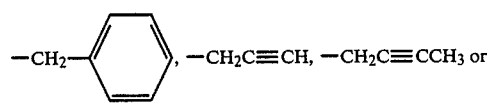

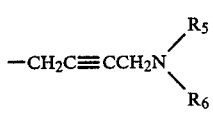

$R_5$ and $R_6$ being independently loweralkyl or alternatively the group $-NR_5R_6$ as a whole being

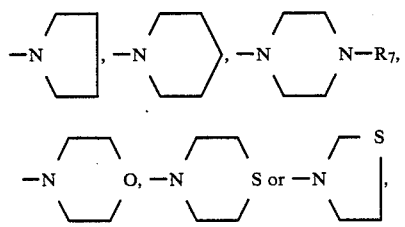

$R_7$ being hydrogen, loweralkyl or arylloweralkyl; which are useful for enhancing cholinergic activity in mammals and hence for the treatment of various memory dysfunctions characterized by decreased cholinergic function such as Alzheimer's disease; to pharmaceutical compositions comprising an effective amount of such a compound and a method of treating patients suffering from memory dysfunction characterized by decreased cholinergic function such as Alzheimer's disease, which comprises administration to the patient an effective amount of such a compound.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, sec-butoxy, t-butoxy and straight- and branched-chain pentoxy and hexoxy.

The term aryl in each occurrence denotes a group having the formula

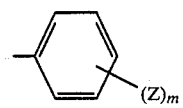

where m is 0, 1, 2 or 3 and each Z is independently loweralkyl, loweralkoxy, halogen, hydroxy, $CF_3$, $NO_2$ or CN, the term halogen signifying fluorine, chlorine, bromine or iodine.

The compounds of the invention are prepared by following one or more of the steps described below. Throughout the description of the synthetic steps, the definitions of $R_1$ through $R_7$ are as given above unless otherwise stated or indicated.

STEP A

A compound of formula II where $R_8$ is loweralkyl is reacted with a strong base such as NaH and the resultant anion is reacted with a compound of formula III where $R_9$ is H or $CH_3$ to afford a compound of formula IV.

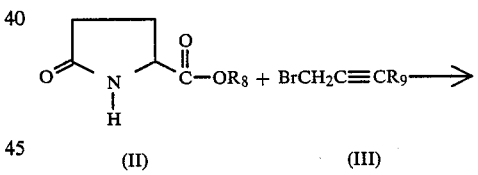

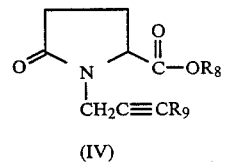

The anion formation reaction is typically conducted by adding a solution of compound II in a suitable solvent such as anhydrous toluene to a suspension of NaH in a suitable medium such as anhydrous toluene. The second step mentioned above is conducted by adding to the above mixture a solution of compound III in a suitable solvent such as toluene and stirring the resultant mixture at a temperature of about $-10°$ to $30°$ C.

STEP B

Compound II is reacted with a strong base such as NaH and the resultant anion is reacted with allyl bromide to afford a compound of formula V.

(II) + BrCH₂CH=CH₂ ⟶

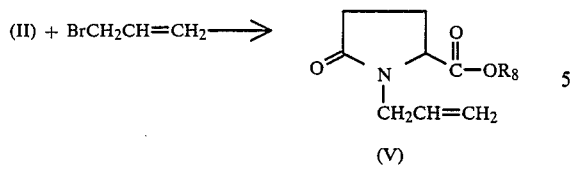

(V)

This reaction is conducted in substantially the same manner as in STEP A described above.

STEP C

Compound II is reacted with a strong base such as NaH and the resultant anion is reacted with benzyl bromide to afford a compound of formula VI.

(II) + BrCH₂C₆H₅ ⟶

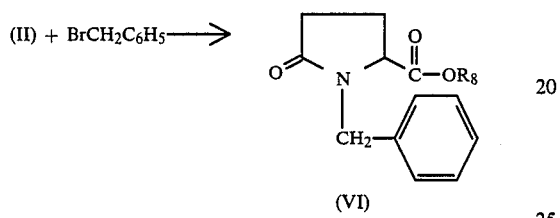

(VI)

This reaction is conducted in substantially the same manner as in STEP A. Synthesis of the compound of formula VI where $R_8$ is methyl is described in E. Campaigne and D. P. Matthews, Journal of Heterocyclic Chemistry, 12, 391 (1975).

STEP D

A compound of formula IVa obtained in STEP A is reacted with paraformaldehyde and an amine of the formula $HNR_5R_6$ to afford a compound of formula VII.

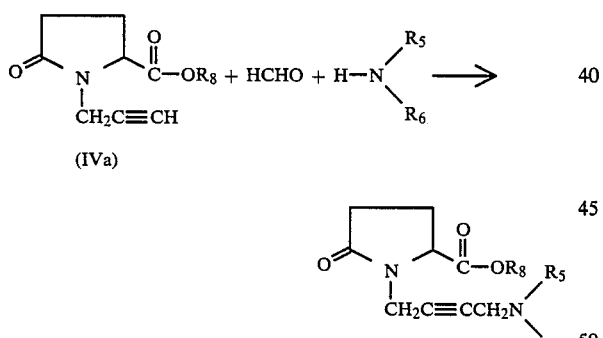

The above reaction is typically conducted in a suitable medium such as anhydrous dioxane in the presence of cuprous chloride and stirring the reaction mixture at a temperature of about 25° C. to 80° C.

STEP E

A compound of formula VIII obtained from one of the foregoing STEPS is reacted with sodium borohydride to afford a compound of formula IX.

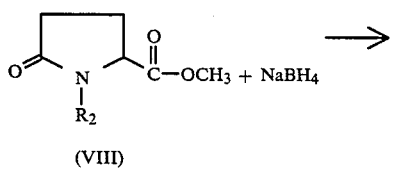

(VIII)

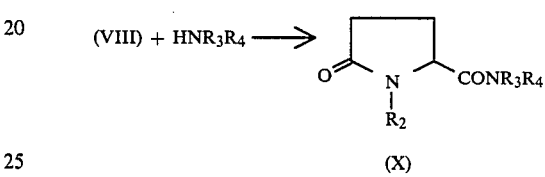

(IX)

This reaction is typically conducted by adding powder form NaBH₄ to a solution of compound VIII in a suitable solvent such as ethanol and stirring the reaction mixture at a temperature of about 10° C. to 50° C.

STEP F

Compound VIII is reacted with ammonia or an amine of the formula $HNR_3R_4$ to afford a compound of formula X.

(VIII) + HNR₃R₄ ⟶

(X)

This reaction is typically conducted by feeding anhydrous ammonia or the amine to a solution of compound VIII in a suitable solvent such as anhydrous methanol preferably at ice temperature and thereafter continuing the reaction at a temperature of about 5° C. to 50° C.

The compounds of formula I of this invention are useful in the treatment of various memory dysfunctions characterized by decreased cholinergic function, such as Alzheimer's disease.

This utility is demonstrated by the ability of these compounds to restore cholinergically deficient memory in the Dark Avoidance Assay, where they are generally active over a broader dose range than heretofore known compounds, a distinct therepeutic advantage.

Dark Avoidance Assay (reference: Z. Bohdanecky & M. E. Jarvik, Int. J. Neuropharmacol. 6,217 (1967))

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animals' initial exposure to the test chamber, the animal re-enters the dark compartment shortly after being placed in the test chamber 24 hours later. This effect of scopolamine is countered by an active test compound, resulting in a greater interval before re-entry into the dark compartment.

The results for active compound are expressed as the percent of a group of animals in which the effect of scopolamine is countered, as manifested by an increased interval between being placed in the test chamber and re-entering the dark compartment.

The results of a representative compound of this invention are presented in Table 1 along with that of physostigmine, a reference compound.

TABLE 1

| Compound | Dose mg/kg body weight s.c. | % of Animals With Scopolamine Induced Memory Deficit Reversed |
|---|---|---|
| (structure: pyrrolidinone with CO$_2$CH$_3$ and N—CH$_2$C≡CH substituents) | 0.63 | 53% |
| Physostigmine | 0.31 | 20% |

Further evidence of cholinergic activity (cholinomimetic) is provided by a compound's ability to produce a contraction in an isolated guinea pig ileum preparation (reference: J. P. Long and C. Y. Chiou, J. Pharmaceutical Sci., 59 133 (1970)).

The method is described below.

METHOD:

Male guinea pigs weighing 350 grams or more are utilized (the weight or food deprivation is not critical to experimental results). The animal is stunned by a blow to the head and exsanguinated. The abdomen is opened and a segment of ileum (10 to 15 cm) proximal to the ileocecal function is removed (A. F. Munro, J. Physiology, 112, 84 (1951)) and placed in a culture dish and immersed with Krebs solution. Sections of ileum are then cut 3 cm in length and thoroughly rinsed.

The rinsed segment is slid on the thick section of a Pasteur pipette. Using a wet Q-tip with Krebs, the tissue is stroked tangentially into the mesentary border along the length of the segment. Gradually, the thin grey longitudinal muscle will pull away. Continue stroking tangentially all around the segment. The longitudinal muscle will easily pull away upon completion. If there is any resistance, cut along the mesentary border. The strip is then placed in clean Krebs solution. Four-O silk is secured to each end making a 1.5 to 2 cm strip. The strip is then ready for hanging in the bath bubbled with 95% O$_2$ and 5% CO$_2$. The bath temperature is maintained at 37° C. About 0.5 to 1.0 grams of tension is applied and the tissue is left to equilibrate for one hour.

When testing for cholinergic compounds, the tissues are challenged with acetylcholine chloride at $2.7 \times 10^{-5}$M after one hour. The response must be greater than seven decigrams. A tissue cannot be used if the response to acetylcholine is equal to or less than seven decigrams. N=3 tissues will be recognized to be taken from one or more guinea pigs.

The Krebs bicarbonate solution is made in the following manner and chlorpheniramine is added to antagonize endogenous histamine:

| Compound | Final Concentration | 4 L Stock Sol. |
|---|---|---|
| NaCl | 118 mM | 276 grams |
| KCl | 4.7 mM | 14.0 grams |
| CaCl$_2$ | 2.54 mM | 14.8 grams |
| KH$_2$PO$_4$ | 1.2 mM | 6.4 grams |
| MgSO$_4$.7H$_2$O | 1.2 mM | 5.6 grams |
| NaHCO$_3$ | 26.0 mM | * |
| Glucose | 11.5 mM | * |
| Chloropheniramine | $1.25 \times 10^{-6}$ M | 1.92 mg |

*To each 100 mls of stock solution add 2.0 grams of glucose and 2.1 grams of NaHCO$_3$ and QS to 1000 mls, with distilled H$_2$O.

Results of a representative compound of this invention are presented in Table 2 along with that of carbachol, a reference compound.

TABLE 2

| Compound | Guinea Pig Ileum % Contraction at [M] Concentration |
|---|---|
| (structure: pyrrolidinone with CO$_2$CH$_3$ and N—CH$_2$C≡CH substituents) | 50% at $7.2 \times 10^{-6}$ |
| carbachol | 50% at $1.3 \times 10^{-7}$ |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention my be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared such that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposible syringes or multiple dose vials made of glass or plastic.

Examples of the compounds of this invention include:
5-methoxycarbonyl-1-(2-propynyl)-2-pyrrolidinone;
5-hydroxymethyl-1-(2-propynyl)-2-pyrrolidinone;
5-oxo-1-(2-propynyl)-2-pyrrolidine carboxamide;
5-methoxycarbonyl-1-[4-(1-pyrrolidinyl)-2-butynyl]-2-pyrrolidinone;
5-oxo-1-[4-(1-pyrrolidinyl)-2-butynyl]-2-pyrrolidine carboxamide;
5-methoxycarbonyl-1-[4-(1-piperidinyl)-2-butynyl]-2-pyrrolidinone;
5-oxo-1-[4-(1-piperidinyl)-2-butynyl]-2-pyrrolidine carboxamide;
5-methoxycarbonyl-1-[4-(4-methyl-1-piperazinyl)-2-butynyl]-2-pyrrolidinone;
1-[4-(4-methyl-1-piperazinyl)-2-butynyl]-5-oxo-2-pyrrolidine carboxamide;
5-methoxycarbonyl-1-[4-(1-morpholinyl)-2-butynyl]-2-pyrrolidinone;
1-[4-(1-morpholinyl)-2-butynyl]-5-oxo-2-pyrrolidine carboxamide;
1-(2-butynyl)-5-methoxycarbonyl-2-pyrrolidinone;
5-methoxycarbonyl-1-(2-propenyl)-2-pyrrolidinone; and
5-hydroxymethyl-1-phenylmethyl-2-pyrrolidinone.

The following examples are presented in order to illustrate this invention.

EXAMPLE 1

5-Methoxycarbonyl-1-(2-propynyl)-2-pyrrolidinone

Sodium hydride (45.20 g of a 50% suspension in mineral oil) was washed with sieve dried toluene (4×300 ml). After decantation, sieve dried toluene (1000 ml) was added to the NaH. The stirred suspension was treated dropwise with a solution of 129.12 g of methyl pyroglutamate in sieve dried toluene (100 ml). The flask was immersed during this time in an oil bath which served as a heat sink. After the addition of the methyl pyroglutamate solution was complete, the bath temperature was raised to 65° C. The solution was maintained at 65° C. for 30 minutes, chilled to −1° C. and then treated dropwise with 132.75 g of 80 weight % solution of propargyl bromide in toluene. After the addition was complete, the ice bath was removed and the mixture was stirred overnight at ambient temperature.

Celite was added to the mixture and the mixture was vacuum filtered through a Celite pad. The filtrate was concentrated to a yellow oil. The oil was extracted with hexane (2×150 ml) and again concentrated to a yellow oil. Purification by distillation gave 71.95 g of a slightly yellow oil, bp 116° C./0.07 mm Hg, which crystallized on standing (mp 39°–41° C.). The crystals were dried on an unglazed tile plate.

ANALYSIS: Calculated for $C_9H_{11}NO_3$: 59.66% C, 6.12% H, 7.73% N. Found: 59.58% C, 6.24% H, 7.58% N.

EXAMPLE 2

5-Hydroxymethyl-1-(2-propynyl)-2-pyrrolidinone

To an ice-water chilled solution of 6.42 g of 5-methoxycarbonyl-1-(2-propynyl)-2-pyrrolidinone in absolute ethanol (60 ml), 1.55 g of powdered sodium borohydride was added. The mixture was stirred overnight at ambient temperature.

The reaction was quenched by the addition of concentrated hydrochloric acid to pH 5, at which time a precipitate formed. The mixture was vacuum filtered and the filtrate was concentrated to a colorless oily solid. The material was dissolved in toluene and concentrated to remove any water that was present.

Purification was accomplished by high performance liquid chromatography (HPLC hereinafter; silica gel, eluted with ethyl acetate). The appropriate fractions were combined and concentrated to a colorless solid. The solid was recrystallized twice from ethyl acetate/hexane (1:2) to yield 2.56 g of colorless crystals, mp 60°–61.5° C.

ANALYSIS: Calculated for $C_8H_{11}NO_2$: 62.72% C, 7.24% H, 9.15% N. Found: 62.44% C, 7.03% H, 9.12% N.

EXAMPLE 3

5-Oxo-1-(2-propynyl)-2-pyrrolidine carboxamide

An ice water chilled solution of 5-methoxycarbonyl-1-(2-propynyl)-2-pyrrolidinone (5.1 g) and sieve dried methanol (250 ml) was treated with anhydrous ammonia for ten minutes and was then allowed to stand overnight at ambient temperature. The solution was concentrated to afford an oil which crystallized (4.81 g). Recrystallization from 95% ethanol (20 ml) gave 3.07 g of almost colorless crystals, mp 145°–147° C.

ANALYSIS: Calculated for $C_8H_{10}N_2O_2$: 57.82% C, 6.07% H, 16.86% N. Found: 57.58% C, 6.35% H, 16.86% N.

EXAMPLE 4

5-Methoxycarbonyl-1-[4-(1-pyrrolidinyl)-2-butynyl]-2-pyrrolidinone oxalate

A stirred mixture of pyrrolidine (2.35 g), sieve dried dioxane (15 ml), 5-methoxycarbonyl-1-(2-propynyl)-2-pyrrolidinone (5.44 g), paraformaldehyde (1.08g) and cuprous chloride (0.1g) was placed in a preheated (54° C.) oil bath. After 20 minutes an aliquot was examined by TLC (silica gel, ethyl acetate) which indicated the presence of starting material. The bath temperature was raised to 80° C., a little more pyrrolidine was added and the mixture was stirred for 20 min. TLC analysis indicated complete conversion to a lower $R_f$ material. The mixture was diluted with water (100 ml), acidified with 5% hydrochloric acid and extracted with ether (2×100 ml). The aqueous phase was made alkaline with solid Na$_2$CO$_3$ with cooling and was extracted with CH$_2$Cl$_2$(2×200 ml). The combined and dried (Na$_2$SO$_4$) organic phase was filtered and concentrated to an oil (7.33 g). The oxalate salt was obtained as a solid and was recrystallized from propionitrile to give 3.13 g of a colorless solid, mp 108.5°–112° C.

ANALYSIS: Calculated for C$_{14}$H$_{20}$N$_2$O$_3$.C$_2$H$_2$O$_4$: 54.23% C, 6.26% H, 7.90% N. Found: 53.88% C, 6.24% H, 7.87% N.

EXAMPLE 5

5-Oxo-1-[4-(1-pyrrolidinyl)-2-butynyl]-2-pyrrolidine carboxamide

An ice water chilled solution of 5-methoxycarbonyl-1-[4-(1-pyrrolidinyl)-2-butynyl]-2-pyrrolidinone (5.52 g) in sieve dried methanol (175 ml) was treated with anhydrous ammonia for fifteen minutes and was allowed to stand at ambient temperature overnight. The solution was concentrated to a brown solid (3.33 g). The solid was recrystallized from toluene (100 ml) to give 2.03 g of slightly brown crystals, mp 146°–147.5° C.

ANALYSIS: Calculated for C$_{13}$H$_{19}$N$_3$O$_2$: 62.57% C, 7.62% H, 16.85% N. Found: 62.37% C, 7.61% H, 16.94% N.

EXAMPLE 6

5-Methoxycarbonyl-1-[4-(1-piperidinyl)-2-butynyl]-2-pyrrolidinone oxalate

A flask was charged sequentially with piperidine (6.00 g), sieve dried dioxane (50 ml), 5-methoxycarbonyl-1-(2-propynyl)-2-pyrrolidinone (12.86 g), paraformaldehyde (2.80 g) and cuprous chloride (0.30 g). The stirred mixture was immersed in a preheated oil bath (54° C.). When a TLC (silica gel, methanol) analysis indicated the absence of starting material, the bath temperature was increased to 80° C. and the solution was heated for 1 hour.

The flask was then removed from the oil bath. The solution was diluted with water (300 ml), acidified with 5% HCl (pH<1) and extracted with diethyl ether (3×150 ml). The aqueous phase was basified with sodium carbonate (pH 8) and extracted with dichloromethane (3×150 ml). The organic phase was dried (Na$_2$SO$_4$) overnight. The mixture was vacuum filtered and concentrated to an amber oil (22.40 g).

Purification was partially achieved by HPLC (silica gel, methanol) to give 10.0 g of an amber oil. The oxalate salt formation was achieved by dissolving oxalic acid (0.80 g) in methanol (15 ml) and adding to it a solution of said oil (2.50 g) in methanol (15 ml). The resultant solution was concentrated to afford a white solid (3.12 g) which was recrystallized from absolute ethanol to give 2.20 g of a white solid, mp 140°–141° C.

ANALYSIS: Calculated for C$_{15}$H$_{22}$N$_2$O$_3$.C$_2$H$_4$O$_4$: 55.38% C, 6.52% H, 7.60% N. Found: 55.38% C, 6.71% H, 7.51% N.

EXAMPLE 7

5-Oxo-1-[4-(1-piperidinyl)-2-butynyl]-2-pyrrolidine carboxamide

An ice water chilled solution of 5-methoxycarbonyl-1-[4-(1-piperidinyl)-2-butynyl]-2-pyrrolidinone (5.44 g) in sieve dried methanol (175 ml) was treated with anhydrous ammonia for fifteen minutes and was allowed to stand at ambient temperature overnight. The solution was concentrated to a brown solid (5.00 g). The solid was recrystallized from toluene (125 mL) to give 3.85 g of slightly brown crystals, mp 143°–145° C.

ANALYSIS: Calculated for C$_{14}$H$_{21}$N$_3$O$_2$: 63.82% C, 8.04% H, 15.97% N. Found: 63.63% C, 8.30% H, 15.67% N.

EXAMPLE 8

5-Methoxycarbonyl-1-[4-(4-methyl-1-piperazinyl)-2-butynyl]-2-pyrrolidinone

A stirred mixture of N-methylpiperazine (7.0 g), 5-methoxycarbonyl-1-(2-propynyl)-2-pyrrolidinone (12.86 g), paraformaldehyde (2.8 g), cuprous chloride (0.3 g) and anhydrous dioxane (50 ml) was held for 30 min at 58° C. Thin layer chromatographic analysis (silica gel, methanol) indicated the presence of the starting pyrrolidinone. The mixture was treated with a little N-methylpiperazine and heated to 80° for one hour. The mixture was decanted into water (300 ml), acidified with 5% hydrochloric acid solution and extracted with ether (3×200 ml). The aqueous phase was basified by portionwise addition of solid sodium carbonate and extracted with dichloromethane (4×150 ml). The combined and dried (Na$_2$SO$_4$) organic phase was filtered and concentrated to afford an oil. The oil was purified by preparative HPLC (silica gel, methanol as eluent) to give 9.84 g of the product as an oil.

EXAMPLE 9

1-[4-(4-Methyl-1-piperazinyl)-2-butynyl]-5-oxo-2-pyrrolidine carboxamide dihydrate An ice water chilled solution of 5-methoxycarbonyl-1-[4-(4-methyl-1-piperazinyl)-2-butynyl]-2-pyrrolidinone (5.02 g) in sieve dried methanol (150 ml) was treated with anhydrous ammonia for fifteen minutes and was allowed to stand at ambient temperture overnight. The solution was concentrated to an amber oil.

Purification by HPLC (silica gel, methanol) gave approximately 3.5 g of an amber oil which crystallized upon standing. The solid was recrystallized from toluene (100 ml) to afford 2.35 g of slightly brown crystals, mp, 124°–125.5° C.

ANALYSIS: Calculated for C$_{14}$H$_{22}$N$_4$O$_2$.2H$_2$O: 53.46% C, 8.34% H, 17.83% N. Found: 53.24% C, 8.38% H, 17.71% N.

EXAMPLE 10

5-Methoxycarbonyl-1-[4-(1-morpholinyl)-2-butynyl]-2-pyrrolidinone oxalate

A flask was charged sequentially with morpholine (7.84 g), sieve dried dioxane (50 ml), 5-methoxycarbonyl-1-(2-propynyl)-2-pyrrolidinone (16.62 g), paraformaldehyde (3.30 g) and cuprous chloride (0.30 g). The stirred mixture was immersed in a preheated oil bath (54° C.). When a TLC (silica gel, methanol) analysis indicated the absence of starting material, the bath temperature was raised to 80° C. and the solution was heated for 75 minutes.

The flask was then removed from the oil bath. The solution was diluted with water (30 ml), acidified with 5% HCl (pH 1) and extracted with diethyl ether (4×150 ml). The aqueous phase was basified with sodium carbonate (pH 8) and extracted with dichloromethane (4×150 ml). The organic phases were combined, dried (Na$_2$SO$_4$), vacuum filtered and concentrated to an amber oil (22 g). TLC (silica gel, methanol) analysis indicated the oil was quite pure. The oxalate salt formation was achieved by dissolving oxalic acid (1.90 g) in methanol (30 ml) and adding a solution of the oil (6.00 g) in methanol (30 ml). The resultant solution was concentrated to an amber oil which was treated with absolute ethanol and the solution was concentrated to an amber oil which solidified on standing (6 g). The solid was recrystallized from proprionitrile (100 ml) to give 3.21 g of a slightly brown solid, mp 89°–90° C. The solid was dried overnight under vacuum at 40° C.

ANALYSIS: Calculated for $C_{14}H_{20}N_2O_4 \cdot C_2H_2O_4$: 51.86% C, 5.99% H, 7.57% N. Found: 51.33% C, 6.14% H, 7.52% N.

EXAMPLE 11

1-[4-(1-Morpholinyl)-2-butynyl]-5-oxo-2-pyrrolidine carboxamide

An ice water chilled solution of 5-methoxycarbonyl)-1-[4-(1-morphlinyl)-2-butynyl]-2-pyrrolidinone (6.00 g) in sieve dried methanol (200 ml) was treated with anhydrous ammonia for fifteen minutes and was allowed to stand at ambient temperature overnight. The solution was concentrated to an amber oil which solidified on standing (5 g). The solid was recrystallized twice from toluene (100 ml) to give 2.11 g of colorless crystals, mp 131°–132° C.

ANALYSIS: Calculated for $C_{13}H_{19}N_3O_3$: 58.82% C, 7.22% H, 15.85% N. Found: 58.97% C, 7.30% H, 15.87% N.

EXAMPLE 12

1-(2-Butynyl)-5-methoxycarbonyl-2-pyrrolidinone

Sodium hydride (5.40 g of a 50% suspension in mineral oil) was washed with sieve dried toluene (3×100 ml) After decantation, sieve dried toluene (100 ml) was added to the NaH. The stirred suspension was treated dropwise with a solution of 16.17 g of methyl pyroglutamate in sieve dried toluene (20 ml). The flask was immersed during this time in an oil bath which served as a heat sink. After the addition of the methyl proglutamate solution was complete, the bath temperature was raised to 70° C. The solution was then cooled to ambient temperature and treated dropwise with 10.01 g of 1-chloro-2-butyne[1] in toluene (10 ml). The mixture was stirred at room temperature for 2.5 hours and then vacuum filtered. The filtrate was concentrated to an amber oil.

REFERENCE: 1. M. G. Ettlinger and J. E. Hodgkins, J. Amer. Chem. Soc. 77, 1831 (1955).

Purification was accomplished by HPLC (silica gel, eluted with ethyl acetate). Appropriate fractions were combined and concentrated to a yellow oil which solidified on standing. The solid was recrystallized from cyclohexane (35 ml) to afford 2.29 g of colorless crystals, mp 48°–52.5° C.

ANALYSIS: Calculated for $C_{10}H_{13}NO_3$: 61.50% C, 6.72% H, 7.18% N. Found: 61.01% C, 6.72% H, 7.07% N.

EXAMPLE 13

5-Methoxycarbonyl-1-(2-propenyl)-2-pyrrolidinone

Sodium hydride (13.44 g of a 50% suspension in mineral oil) was washed with sieve dried toluene (3×150 ml). After decantation, sieve dried toluene (500 ml) was added to the NaH. The stirred suspension was treated dropwise over one hour with a solution of methyl pyroglutamate (35.79 g) in sieve dried toluene (50 ml). The flask was immersed during this time in an oil bath which served as a heat sink. After the addition of the methyl pyroglutamate solution was complete, the bath temperature was raised to 80° C. (65° C. internal temperature) and heated for 0.5 hour. The flask was then cooled to 0° C. and a solution of allyl bromide (33.87 g) in sieve dried toluene (20 ml) was added dropwise over a 10 minute period to the solution. After the addition was complete, the flask was warmed to ambient temperature and stirred overnight.

The mixture was vacuum filtered and the filtrate was concentrated to a slightly yellow oil. Purification by HPLC (silica gel, eluted with ethyl acetate) yielded 10.20 g of a slightly yellow oil. The sample was dried in an Abderhalden pistol over toluene for 45 minutes.

ANALYSIS: Calculated for $C_9H_{13}NO_3$: 58.98% C, 7.16% H, 7.65% N. Found: 58.66% C, 7.14% H, 7.47% N.

EXAMPLE 14

5-Hydroxymethyl-1-phenylmethyl-2-pyrrolidinone

To an ice-water chilled solution of 7.0 g of 5-methyloxycarbonyl-1-methylphenyl-2-pyrrolidinone (prepared according to the method described by E. Campaigne & D. P. Matthews, J. Heterocyclic Chemistry 12, 391 (1975)) in absolute ethanol (100 ml) was added 1.13 g of powdered sodium borohydride. The mixture was stirred overnight at ambient temperature. The reaction was quenched by the addition of concentrated hydrochloric acid to pH 5. The solution was concentrated to a clear colorless oil which was stored under refrigeration overnight.

Purification was accomplished by HPLC (silica gel, eluted with ethyl acetate). The appropriate fractions were combined and concentrated to give a colorless solid. The solid was recrystallized from ethyl acetate/hexane (1:1) to yield 3.29 g of colorless crystals, mp 74°–76° C.

ANALYSIS: Calculated for $C_{12}H_{15}NO_2$: 70.22% C, 7.37% H, 6.83% N. Found: 69.98% C, 7.49% H, 6.71% N.

I claim:

1. A compound having the formula,

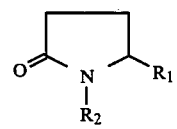

where $R_1$ is —CH$_2$OH; and $R_2$ is —CH$_2$CH=CH$_2$,

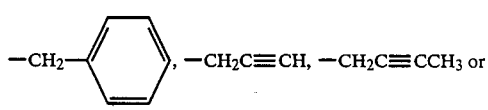

—CH$_2$C≡CCH$_2$N

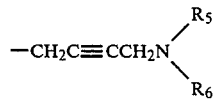

$R_5$ and $R_6$ being independently loweralkyl or alternatively the group —NR$_5$R$_6$ as a whole being

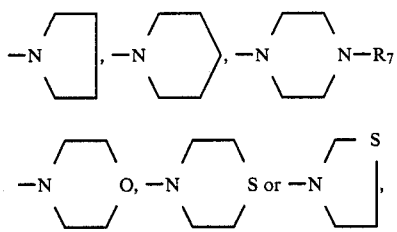

R₇ being hydrogen, loweralkyl or arylloweralkyl; or a pharmaceutically acceptable acid addition salt thereof.

2. A compound of the formula

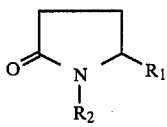

where $R_1$ is loweralkoxycarbonyl, —CH₂OH or —CONR₃R₄, $R_3$ and $R_4$ being independently hydrogen, loweralkyl or arylloweralkyl; and $R_2$ is —CH₂CH=CH₂ or

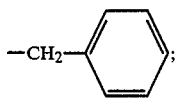

or a pharmaceutically acceptable addition salt thereof.

3. The compound as defined in claim 1, where $R_2$ is

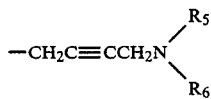

4. The compound as defined in claim 3, wherein the group —NR₅R₆ as a whole is

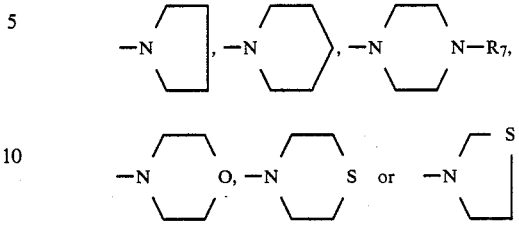

R₇ being hydrogen, loweralkyl or arylloweralkyl.

5. The compound as defined in claim 1, which is 5-hydroxymethyl-1-(2-propynyl)-2-pyrrolidinone.

6. The compound as defined in claim 2, which is 5-methoxycarbonyl-1-(2-propenyl)-2-pyrrolidinone.

7. The compound as defined in claim 1, which is 5-hydroxymethyl-1-phenylmethyl-2-pyrrolidinone.

8. A pharmaceutical composition which comprises a compound as defined in claim 1 in an amount effective for alleviating memory dysfunction characterized by decreased cholinergic function and a suitable carrier therefor.

9. A pharmaceutical composition which comprises a compound as defined in claim 2 in an amount effective for alleviating memory dysfunction characterized by decreased cholinergic function and a suitable carrier thereof.

10. A method of treating a pateint suffering from memory dysfunction characterized by decreased cholinergic function which comprises administering an effective amount of a compound as defined in claim 1.

11. A method of treating a patient suffering from memory dysfunction characterized by decreased cholinergic function which comprises administering an effective amount of a compound as defined in claim 2.

* * * * *